(12) United States Patent
Bremer et al.

(10) Patent No.: US 7,127,956 B2
(45) Date of Patent: Oct. 31, 2006

(54) METHOD OF SAMPLE DELIVERY FOR A SAMPLE ANALYZER AND LINER HANDLING SYSTEM

(75) Inventors: Ralf Bremer, Oberhausen (DE); Bernhard Rose, Dusseldorf (DE)

(73) Assignee: Gerstel Systemtechnik GmbH & Co. KG, Mulheim (DE)

( * ) Notice: Subject to any disclaimer, the term of this patent is extended or adjusted under 35 U.S.C. 154(b) by 0 days.

(21) Appl. No.: 11/096,730

(22) Filed: Apr. 1, 2005

(65) Prior Publication Data
US 2005/0229723 A1   Oct. 20, 2005

(30) Foreign Application Priority Data
Apr. 5, 2004   (DE) ...................... 10 2004 016 670

(51) Int. Cl.
*G01N 1/00* (2006.01)
(52) U.S. Cl. ................................... 73/864.31
(58) Field of Classification Search ............. 73/864.31, 73/23.41, 23.42, 863.11, 863.12, 864.81; 96/413, 101; 95/82
See application file for complete search history.

(56) References Cited
U.S. PATENT DOCUMENTS
4,543,838 A * 10/1985 Fohler ..................... 73/864.31
6,245,298 B1 * 6/2001 Bremer et al. ................ 422/80
2003/0233893 A1 * 12/2003 Bremer et al. ........... 73/864.21

* cited by examiner

Primary Examiner—Robert Raevis
(74) Attorney, Agent, or Firm—Patterson, Thuente, Skaar & Christensen, P.A.

(57) ABSTRACT

The invention relates to a method of sample delivery for a sample analyser, which has a delivery device for samples which can be loaded with exchangeable liners, which are tubular at least at the inlet end and hold the sample, the liners, on which there is respectively fitted at the gas inlet end a transporting head which holds the liner by means of a seal hereby having a friction fit, being arranged such that they are inserted at predetermined locations in a magazine and/or in sample containers, a changing device, which is equipped with a gripper for the transporting heads of the liners, being used and on the basis of a predetermined program, the changing device gripping the respective liner at a predetermined place on its transporting head and inserting it into the delivery device in a sealing manner, the sample delivery being performed and, subsequently, the liner being removed from the delivery device by the changing device, by gripping its transporting head, and also to a liner handling system for this.

1 Claim, 4 Drawing Sheets

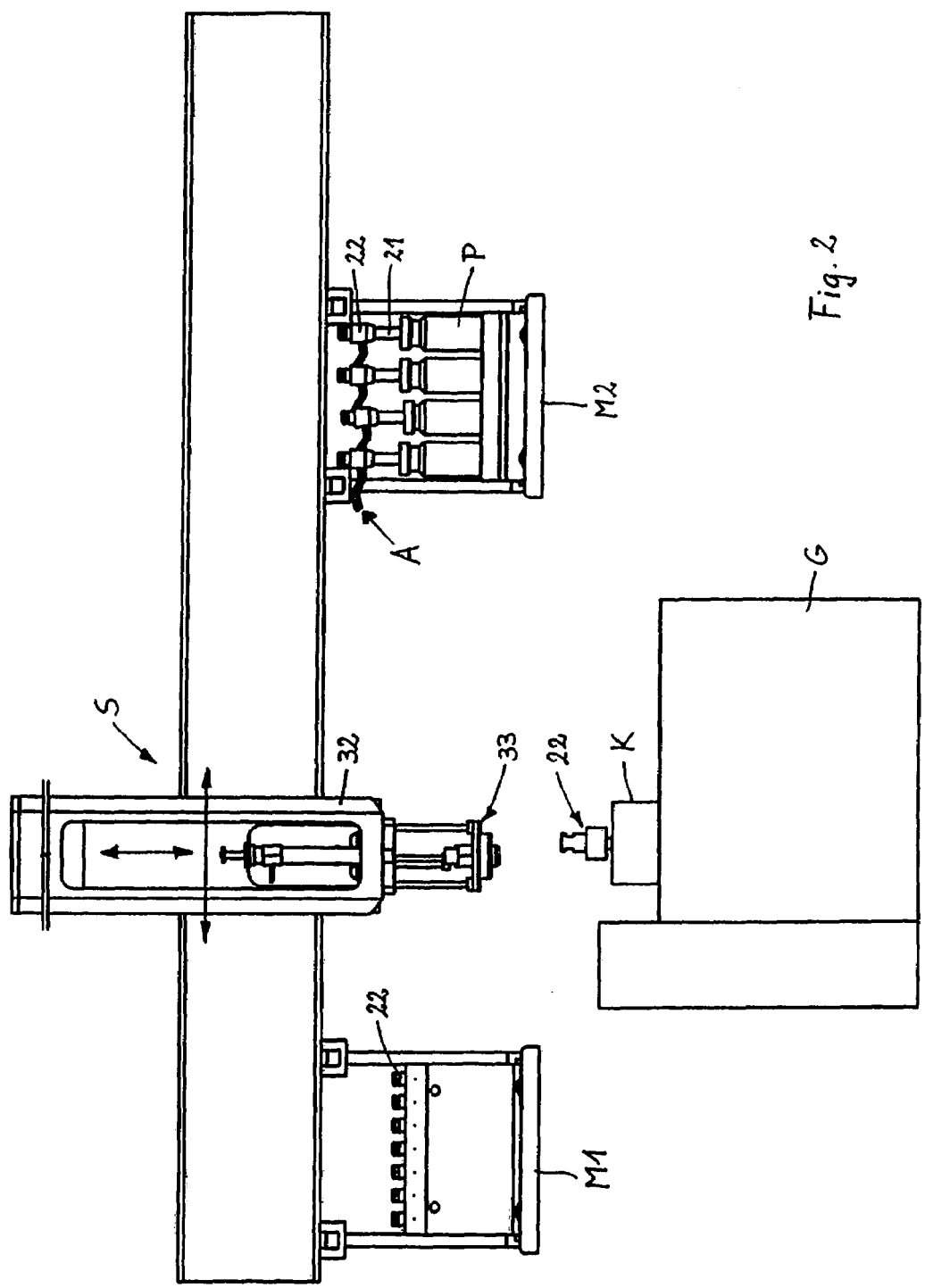

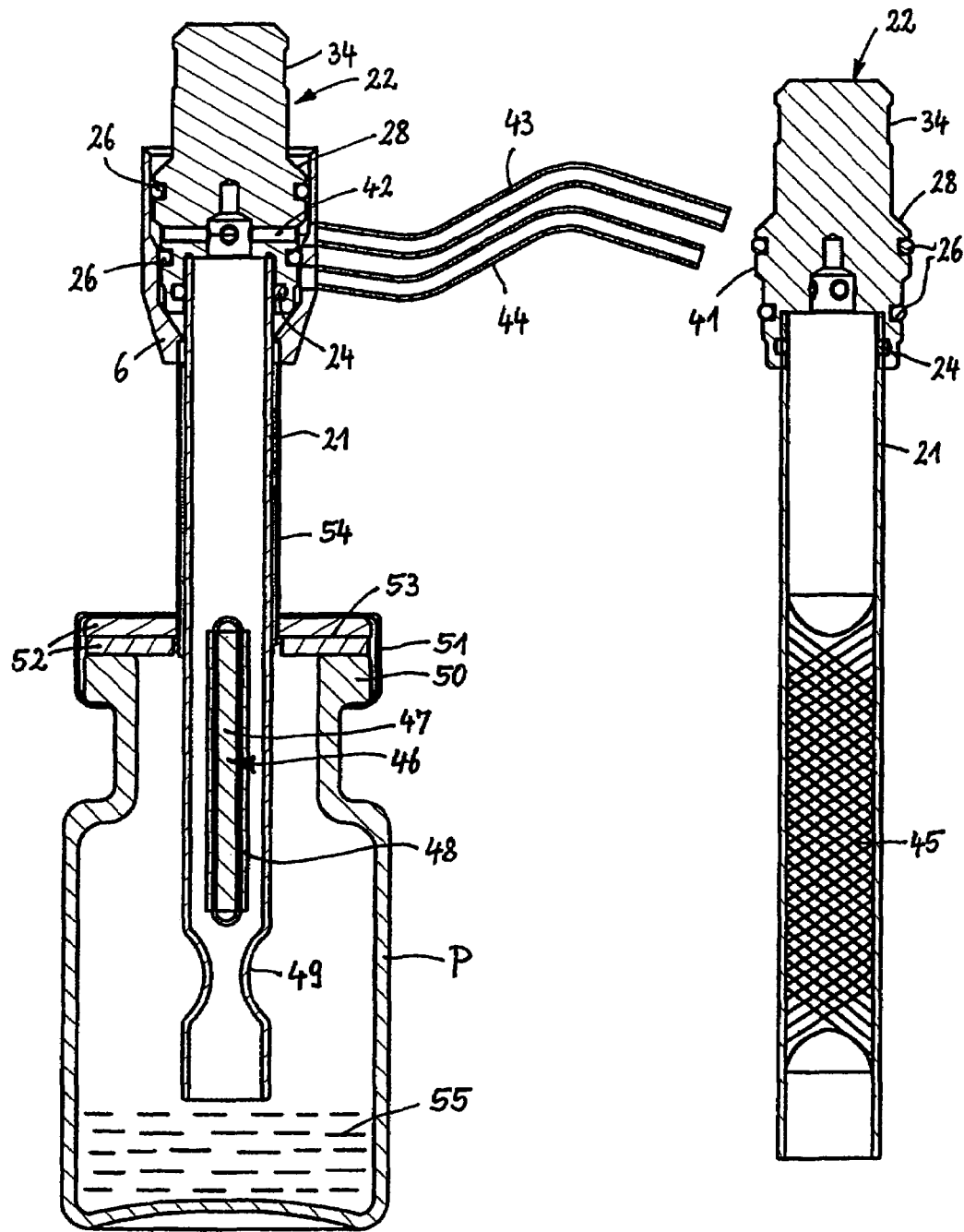

METHOD OF SAMPLE DELIVERY FOR A SAMPLE ANALYZER AND LINER HANDLING SYSTEM

FIELD OF THE INVENTION

The invention relates to a method of sample delivery for a sample analyser and to a liner handling system as well as components thereof for the use in connection with sample analysers as chromatographic systems.

BACKGROUND OF THE INVENTION

In gas chromatography, samples for sample analysis are introduced into the gas chromatograph by means of delivery devices, the samples being held by exchangeable tubular sample containers, known as liners, through which carrier gas can flow. Although customary liners can be specifically designed or equipped for holding the samples inside them, on the outside they are of a standardized cylindrical design—possibly apart from a constriction at the outlet end—and smooth and are generally in the form of glass or stainless steel tubes.

Since manual liner changing is time-consuming both as an operation in itself and with respect to prolonged uninterrupted operation, it is known to provide liners with special heads which permit automated changing. However, these special liners can then only be used together with specific delivery devices and changers. There is no interchangeability.

WO 00/50885 discloses a liner which is provided at its gas inlet end with a flange on which a septum is arranged, held on the flange by means of a closure cap.

U.S. Pat. No. 5,686,656 discloses use of a liner made larger than standard dimensions together with a liner carrier having a handling flange. In this case, the liner carrier is held on the delivery device by a coupling element.

SUMMARY OF THE INVENTION

It is an object of the invention is to provide a method of sample delivery for a sample analyser which permits automatic liner changing without the use of specially designed liners.

It is a further object of the invention to provide a liner handling system with a sample analyser which permits automatic liner changing without the need of specially designed liners.

It is a further object of the invention to provide a transporting head for a tubular liner which is not specially designed for a distinct line handling system.

It is a further object of the invention to provide a delivery device for samples for a sample analyser without the need of specially designed liners.

It is a further object of the invention to provide a sample container which allows to take up a not specially designed liner provided with a transporting head.

According to the invention, this object is achieved by a method of sample delivery for a sample analyser, which has a delivery device for samples which can be loaded with exchangeable liners, which are tubular at least at the inlet end and hold the sample, the liners, on which there is respectively fitted at the gas inlet end a transporting head which holds the liner by means of a seal hereby having a friction fit, being arranged such that they are inserted at predetermined locations in a magazine and/or in sample containers, a changing device, which is equipped with a gripper for the transporting heads of the liners, being used and on the basis of a predetermined program, the changing device gripping the respective liner at a predetermined place on its transporting head and inserting it into the delivery device in a sealing manner, the sample delivery being performed and, subsequently, the liner being removed from the delivery device by the changing device, by gripping its transporting head.

As a result, customary, commercially available liners that are not specially designed with respect to their transport and are virtually tubular, or at least tubular at the head and/or the inlet end, for instance made of glass or steel, can be used and can at the same time also be employed as a sampler.

Subject of the invention is further a liner handling system with a sample analyser, which has a delivery device for samples which can be loaded with exchangeable liners, which are tubular at least at the inlet end and hold the sample, a magazine for holding liners and a changing device for changing and transporting liners between the delivery device, the magazine and, if appropriate, sample containers on the basis of a predetermined program, there being respectively fitted on the liners, at the gas inlet end, a transporting head which holds the liner by means of a seal hereby having a friction fit, the changing device being equipped with a gripper for the transporting heads of the liners, and the delivery device being provided with a clamping device for the sealing clamping of the transporting head into the delivery device.

Subject of the invention is also a transporting head for a tubular liner which is tubular at least at the inlet end, with an insertion opening, provided with a sealing ring, for holding the liner with a friction fit and with sealing rings located on the outer circumference.

Further, a subject of the invention is a delivery device for samples for a sample analyser, comprising a holding cup with a bottom through-opening for a liner, which is provided with a transporting head which can be held by the holding cup, is tubular at least at the inlet end and is held by the transporting head with a friction fit, and comprising a clamping device for clamping the transporting head into the holding cup.

Additionally, a subject of the invention is a sample container with a flange, which is arranged at the inlet end and on which two septa provided with a through-opening and with a pierceable foil arranged between them are fastened by a cap, it being possible to insert into the through-openings, in a manner sealed from the outside, a guiding tube with a holding cup for a transporting head which holds a liner that is tubular at least at the inlet end by means of a seal hereby having a friction fit.

Further objects, embodiments ans advantages can be taken from the following description.

BRIEF DESCRIPTION OF THE DRAWINGS

The invention is explained in more detail below on the basis of exemplary embodiments that are represented in the accompanying figures.

FIG. 2 schematically shows an embodiment of a set-up for sample preparation and delivery for a gas chromatograph.

FIG. 3 shows a liner with a further embodiment of a transporting head.

FIG. 4 shows a liner with a transporting head according to FIG. 3 together with a sample container.

DETAILED DESCRIPTION OF PREFERRED EMBODIMENTS

Figure 1:
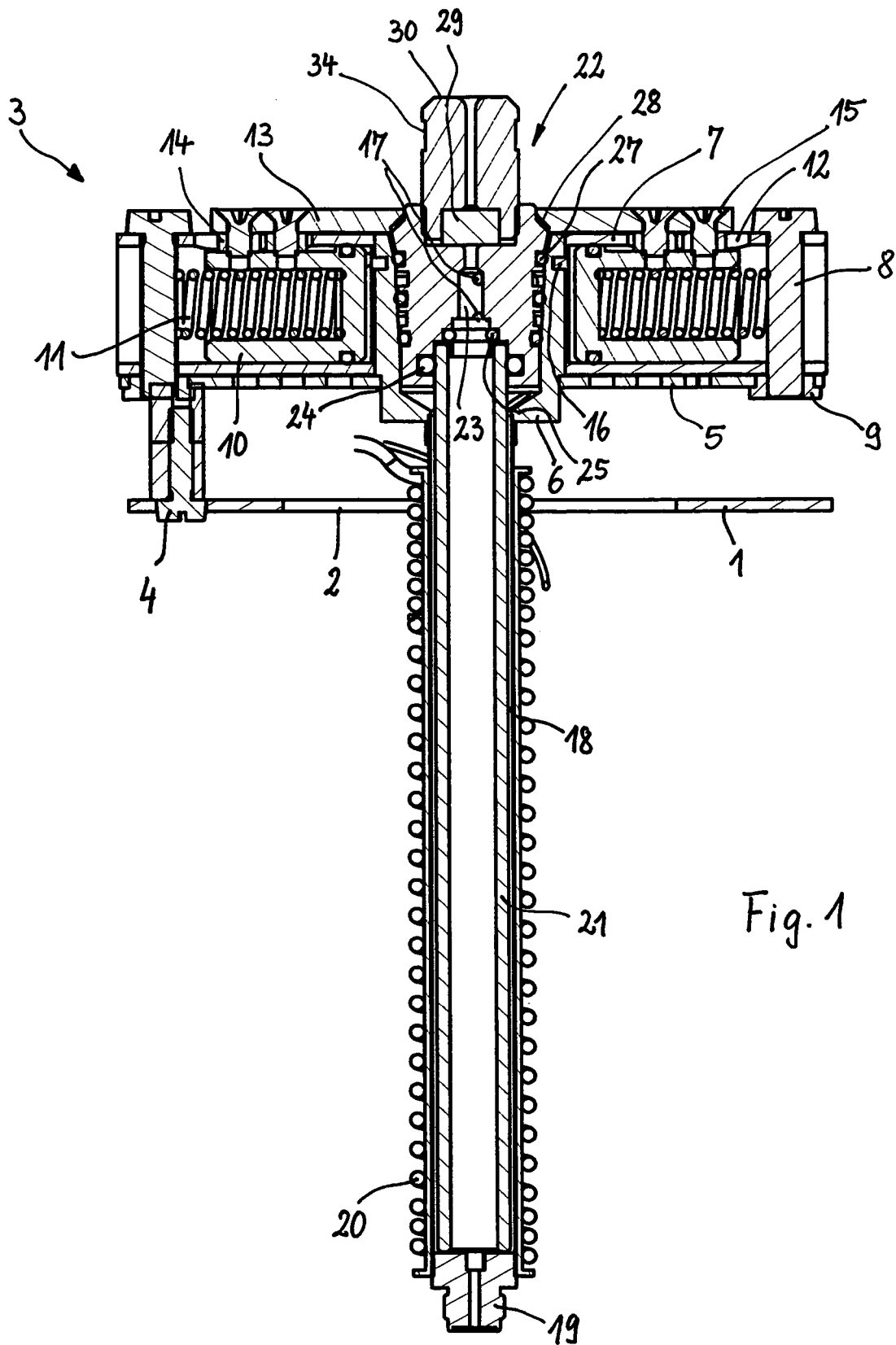
FIG. 1 shows a section through an embodiment of a cold delivery device for a gas chromatograph with an inserted liner.

A cold delivery device K for a gas chromatograph as shown in FIG. 1 comprises a base plate 1 with a through-opening 2, a liner holder 3 being detachably fastened to the base plate 1 at a distance by means of screws 4. The liner holder 3 comprises a round, perforated carrier plate 5, which comprises a central receiving opening for a holding cup 6 fastened therein. Resting on the carrier plate 5 are a number of sleeves 7, which extend radially to the holding cup 6, may have a rectangular or round cross section and are fastened by means of screws 8 and nuts 9. The sleeves 7 each hold a piston 10, which is radially displaceable in them and is biased radially inwards by means of a spring 11 supported on the associated screws 8. The sleeves 7 are provided on the upper side with a slit 12. On the sleeves 7 there is in each case a clamping jaw 13, which is radially displaceable by means of guiding blocks 14 running in the slit 12. The respective clamping jaw 13 is connected to an associated piston 10 by means of screws 15, which also carry the guiding blocks 14. On the outer circumference of the receiving cup 6 there is a peripheral groove 16, to which a pressure medium, in particular compressed air, can be admitted, which is closed off from the outside, outside the region of the sleeves 7, and via which the pistons 10 can be acted on counter to the force of the springs 11, and consequently can be displaced radially inwards together with the clamping jaws 13.

The holding cup 6 is provided with bores 17, opening out inside it, for supplying carrier gas or removing purging gas and at the bottom with an opening, fastened in which is a guiding tube 18, which is provided at the bottom with a connecting piece 19. Fastened on the outside of the guiding tube 18 is a heating device 20, which extends to the connecting piece 19 and is held by the latter. Cooling is also provided (not represented), for example by means of a Peltier element.

The cold delivery device K is designed for holding a liner 21, which is provided with a transporting head 22.

The rotationally symmetrical transporting head 22 has a stepped bore 23, which is arranged in the axial direction and, adjacent to the holding end on the liner side, is provided with a peripheral groove, which receives an O-ring 24. The O-ring 24 engages around the tubular liner 21 with a friction fit, the end of the liner 21 inserted into the transporting head 22 butting against a shoulder 25 of the bore 23. Arranged axially spaced apart on the circumference of the transporting head 22 are two peripheral grooves 26, in the region of which the bores 17 of the holding cup 6 open out. Arranged above, between and below the grooves 26 are O-rings 27, in order to seal the regions of the grooves 26 with respect to one another.

At the end remote from the liner 21, the transporting head 22 is provided with a sloping shoulder 28, with which the correspondingly bevelled clamping jaws 13 come into engagement under the effect of the spring biasing acting on the pistons 10, in order to press the slightly conical transporting head 22 into the correspondingly slightly conical inner space of the holding cup 6, so that the O-rings 27 come into sealing engagement with the inner side of the holding cup 6. The liner 21 itself is thereby held by the guiding tube 18.

On the end face of the transporting head 22 that is remote from the liner 21, a needle guiding piece 30 provided with a needle guiding bore is screwed in, with a septum 29 that can be pierced by an injection needle interposed. In the case of the embodiment of the transporting head 22 that is represented in FIG. 1, it is provided with a septum 29, but it may also be designed without a septum, as described later.

FIG. 2 shows a set-up for sample preparation and delivery for a gas chromatograph G, which is provided with a delivery device K which can hold liners 21 with transporting heads 22, such as those described above for example. Furthermore, there is a magazine M1, which has a multiplicity of blind bores 31 in a predetermined pattern for holding liners 21 with transporting heads 22 in a sealed manner, if it is appropriate to do so. Also provided is a holding frame M2 for sample containers P (vials). The liners 21 can be handled by means of an automatic sample preparation and/or delivery device, known as an autosampler S, which is provided with a horizontally and vertically movable arm which is equipped with a device (not represented) for gripping a syringe and also with a gripper 33 for the transporting heads 22, in particular a gripper which can be actuated electromagnetically. Here, the gripper 33 is expediently designed in such a way that sample preparation or delivery by means of a syringe can be performed through the gripper 33.

The autosampler S is therefore able with its gripper 33 to remove liners 21 without samples from the magazine M1 in a predetermined sequence, by gripping their transporting heads 22, and insert them into the delivery device K of the gas chromatograph G. After each insertion, the autosampler S with a syringe moves on the basis of a predetermined program over an associated sample container P provided with a septum, takes a sample by means of the syringe, moves with the syringe over the transporting head 22 of the liner located in the delivery device K, moves the syringe needle through the septum 29 into the liner 21 and delivers the sample to be investigated into the liner 21 by means of the syringe needle. After that, the syringe needle is pulled out again, while the sample delivery takes place. Finally, the liner 21 is gripped on its transporting head 22 by the gripper 33 at a peripheral groove 34, removed from the delivery device K and placed again in the magazine M1, etc. The liner 21 can be used once or n number of times, so that this procedure is performed each time or after every nth use of the liner 21.

The liners 21 may, however, also already be loaded with a sample to be investigated when they are in the magazine. Here it is expedient for the liners 21 to be held by the magazine M1 in such as way that they are sealed off from the outside in blind bores. The autosampler S in this case removes the liners 21 one after the other, inserts them into the delivery device K, removes them again after sample delivery and returns them to the magazine M1.

Furthermore, it may be provided that the autosampler S removes liners 21 without samples from the magazine M1 and inserts them into corresponding holding heads A of sample containers P, where the liners 21 receive the sample to be investigated in order subsequently to be inserted into the delivery device K.

If appropriate, instead of an autosampler S, a special changing device only for the liner 21 may also be used, possibly together with a customary autosampler S.

The liner 21 may, as represented in FIG. 3, also have a transporting head 22 which is provided with a shoulder 41, underneath which a bore 42 (or a number of bores) which is (are) in connection with the inside of the liner 21, cf. FIG. 4, open(s) out at the outer circumference of the transporting head 22.

The liner 21 may be inserted into a corresponding holding cup 6 of the delivery device K and also, as represented, of a sample container P, the holding cup 6 having a stepped bore, so that, when the transporting head 22 is inserted, an annular space is formed adjacent to the mouth of the bore 42 and a further annular space, which is sealed off with respect to the one annular space by means of the O-rings 26, is formed adjacent to the inserted end of the transporting head 22, which annular spaces are respectively connected to a gas line 43, 44 attached to the holding cup 6, in order if appropriate to carry gas through the sample container P and the liner 21. Accordingly, substances to be investigated can be collected for later analysis not only passively (without gas circulation), but also dynamically on a corresponding phase in the liner 21. In this way the liner 21 functions as a sampler.

For absorbing or adsorbing substances to be investigated, the liner 21 may for example hold a packing 45, cf. FIG. 3, or a collector 46 comprising an essentially rod-shaped carrier 47 with an active coating 48, FIG. 4, which is kept in the liner by means of a constriction 49 to stop it falling out. There are, however, many further possibilities of designing liners 21 for absorbing or adsorbing substances to be investigated that come into consideration here.

In the case of the embodiment of the sample container P that is represented in FIG. 4, it is provided that two septa 52 are provided one above the other on its flange 50 by means of a cap 51, between which septa a thin foil 53, for example an aluminium foil, is clamped in a sealing manner. The holding cup 6 which can be fitted onto the sample container P carries on the underside a tube 54, which can be pushed through the cap 51 and the foil 53, while it comes into sealing engagement with at least one septum 52. The tube 54 allows the liner 21 to be introduced into the sample container P for instance, as represented in FIG. 4, for dynamic headspace extraction, if appropriate, or else for entering the sample 55 that is located in the sample container P, if appropriate.

It is also possible, however, to realize a gas supply to the sample container P via its closure instead of via the transporting head 22.

Delivery devices K which are not equipped for liners 21 with transporting heads 22 generally have, however, a threaded connection piece, which can be used for the purpose of fitting an attachment 60 for the delivery device K, which permits the use of liners 21 with transporting heads 22.

Figures 5, 6:
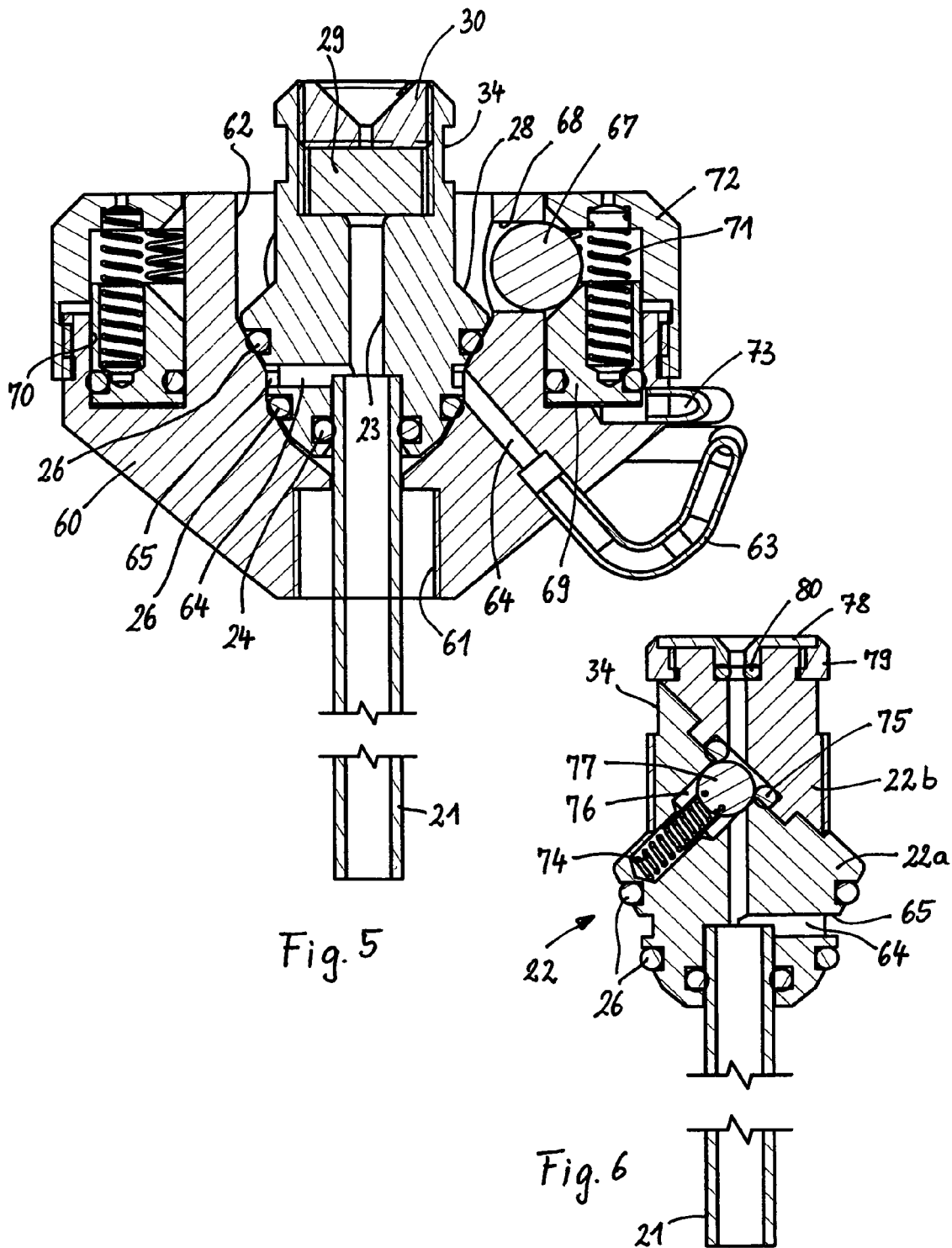
FIG. 5 shows an embodiment of an attachment for a delivery device.
FIG. 6 shows a liner with a modified transporting head.

The embodiment of such an attachment 60 that is represented in FIG. 5 comprises on the underside a bore 61 provided with an internal thread for fastening the attachment 60 on a delivery device K. The transporting head 22 corresponds essentially to that of FIGS. 3 and 4, with this figure additionally depicting the septum 29 and the screwed-in needle guiding piece 30, which are required for the case in which sample delivery is by a syringe, while in the case of the embodiment of FIGS. 3 and 4 the sample is held directly in the sample container P and the sample is delivered directly from the liner 21. The latter may likewise be provided in conjunction with the attachment 60.

The attachment 60 has a recess 62 which corresponds to that of the holding cup 6 and is in connection with the bore 61. Carrier gas can be supplied via a line 63 and a bore 64 as well as a peripheral groove 65 of the transporting head 22 to the inside of the liner 21.

Secure clamping of the transporting head 22 in the attachment 60 is performed here by means of a number of balls 67, which are arranged in a radially displaceable manner in bores 68 of the attachment. Each ball 67 is displaceable in the direction of the shoulder 28 of the transporting head 22 by means of a piston 69 which is bevelled towards the ball 67 and is displaceable in the axial direction of the transporting head. The piston 69 is held in a sealed manner by a bore 70 in the attachment 60 and is biased into its starting position, represented in FIG. 5, by a spring 71, which is supported on a cover 72 of the attachment 60. Compressed air can be applied to the piston 69 via a line 73 on its side that is remote from the ball 67, whereby the ball 67 is pressed into a position on the sloping shoulder 28 of the transporting head 22 such that the latter is kept in engagement with the recess 62 as long as the compressed air is applied to the piston 69.

Since the balls 67 are loosely arranged in the bores 68 (but secured against falling out) in the starting position of the piston 69, they can be pressed outwards when the transporting head 22 is inserted, so that insertion is not hindered.

The embodiment of a transporting head 22 that is represented in FIG. 6 is without a septum. Instead, the bore 23 is closed by a ball 77 which is biased against a sealing ring 75 by means of a spring 74, is displaceable obliquely in relation to the bore 23 in a bore 76 and can be pressed to one side by a syringe needle. When it is inserted, the syringe needle initially comes into sealing engagement at the inlet end with a sealing ring 80 clamped by a cover 78 with a nut 79. For fitting the ball 77, and parts interacting with it, the transporting head 22 comprises two parts 22a, 22b, which are joined together along a sloping surface perpendicularly in relation to the bore 76.

Instead of spring-biasing the pistons 10 and 69, they may also be moved back and forth by means of compressed air.

While the invention has been shown and described with reference to the preferred embodiments, it should be apparent to one ordinary skilled in the art that many changes and modifications may be made without departing from the spirit and scope of the invention.

We claim:

1. A liner handling system with a sample analyzer, which has a delivery device for samples which can be loaded with exchangeable liners, which are tubular at least at a gas inlet end and hold the sample, a magazine for holding liners and a changing device for changing and transporting liners between at least two of the delivery device, the magazine, and sample containers, on the basis of a predetermined program, there being respectively fitted on the liners, at the gas inlet end, a transporting head which holds the liner by means of a seal hereby having a friction fit, the changing device being equipped with a gripper for the transporting heads of the liners, and the delivery device being provided with a clamping device for the sealing clamping of the transporting head into the delivery device.

* * * * *